United States Patent [19]

Angevine et al.

[11] Patent Number: 4,982,040
[45] Date of Patent: Jan. 1, 1991

[54] PROCESS FOR THE CATALYTIC DISPROPORTIONATION OF METHYLNAPHTHALENES

[75] Inventors: Philip J. Angevine, Woodbury; Thomas F. Degnan, Moorestown; David O. Marler, Deptford, all of N.J.

[73] Assignee: Mobil Oil Corp., Fairfax, Va.

[21] Appl. No.: 454,481

[22] Filed: Dec. 21, 1989

Related U.S. Application Data

[63] Continuation-in-part of Ser. No. 254,524, Oct. 6, 1988, and a continuation-in-part of Ser. No. 98,176, Sep. 18, 1987, abandoned, which is a continuation-in-part of Ser. No. 890,268, Jul. 29, 1986, abandoned.

[51] Int. Cl.$^5$ .............................................. C07C 2/00
[52] U.S. Cl. ................................................... 585/475
[58] Field of Search ...................................... 585/475

[56] References Cited

U.S. PATENT DOCUMENTS

| | | | |
|---|---|---|---|
| 3,855,328 | 12/1974 | Hedge | 585/475 |
| 4,418,235 | 11/1983 | Haag et al. | 585/474 |
| 4,439,409 | 3/1984 | Puppe et al. | 502/60 |
| 4,465,253 | 5/1987 | Chu et al. | 585/475 |
| 4,670,615 | 6/1987 | Valyocsik | 585/475 |
| 4,761,514 | 8/1988 | Menard | 585/475 |
| 4,826,667 | 5/1989 | Zones et al. | 423/277 |

FOREIGN PATENT DOCUMENTS

| | | | |
|---|---|---|---|
| 231860 | 8/1987 | European Pat. Off. | 502/64 |
| 293032 | 11/1988 | European Pat. Off. | 502/64 |
| 60-045536A | 3/1985 | Japan | 585/475 |
| 60-092227A | 5/1985 | Japan | 585/475 |

*Primary Examiner*—Anthony McFarlane
*Attorney, Agent, or Firm*—Alexander J. McKillop; Charles J. Speciale; Dennis P. Santini

[57] ABSTRACT

A methylnaphthalene such as 2-methylnaphthalene undergoes catalytic disproportionation to naphthalene and a mixture of dimethylnaphthalene isomers, preferably containing substantial quantities of 2,6-dimethylnaphthalene, employing catalyst comprising zeolite characterized by an X-ray diffraction pattern including interplanar d-spacings at 12.36±0.4, 11.03±0.2, 8.83±0.14, 6.18±0.12, 6.00±0.10, 4.06±0.07, 3.91±0.07 and 3.42±0.06 Angstroms.

19 Claims, No Drawings

PROCESS FOR THE CATALYTIC DISPROPORTIONATION OF METHYLNAPHTHALENES

CROSS-REFERENCE TO RELATED APPLICATIONS

This application is a continuation-in-part of U.S. patent application Ser. No. 254,524, filed Oct. 6, 1988, and a continuation-in-part of U.S. patent application Ser. No. 98,176, filed Sept. 18, 1987, now abandoned, which is a continuation-in-part of U.S. patent application Ser. No. 890,268, filed July 29, 1986 . now abandoned.

BACKGROUND OF THE INVENTION

This invention relates to a process for the catalytic disproportionation of methylnaphthalenes to a mixture of naphthalene and dimethylnaphthalene isomers employing a synthetic porous crystalline material, or zeolite, as disproportionation catalyst.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties. Such molecular sieves, both natural and synthetic, include a wide variety of positive ion-containing crystalline silicates. These silicates can be described as a rigid three-dimensional framework of $SiO_4$ and Periodic Table Group IIIA element oxide, e.g., $AlO_4$, in which the tetrahedra are cross-linked by the sharing of oxygen atoms whereby the ratio of the total Group IIIA element, e.g., aluminum, and silicon atoms to oxygen atoms is 1:2. The electrovalence of the tetrahedra containing the Group IIIA element, e.g., aluminum, is balanced by the inclusion in the crystal of a cation, e.g., an alkali metal or an alkaline earth metal cation. This can be expressed wherein the ratio of the Group IIA element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite Z (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449); zeolite ZSM-20 (U.S. Pat. No. 3,972,983); zeolite ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724, 4,073,865 and 4,104,294 describe crystalline silicates of varying alumina and metal content.

U.S. Pat. Nos. 3,855,328 and 4,418,235 both disclose the disproportionation of methylnaphthalene over a zeolite catalyst to provide a mixture of naphthalene and dimethylnaphthalenes. In the case of U.S. Pat. No. 4,418,235, the zeolite is one having a silica to alumina ratio of at least 12 and a Constraint Index of about 1 to 12, e.g., ZSM-5, ZSM-11, ZSM-12, ZSM-23, ZSM-35 and/or ZSM-38.

Japanese Patent No. J60092227-A appears to describe much the same disproportionation process as U.S. Pat. No. 4,418,235, supra.

Japanese Patent No. J60045536-A appears to disclose the catalyzed transmethylation of methylnaphthalenes to provide dimethylnaphthalenes employing a zeolite catalyst having a silica to alumina ratio of 10–100 and the distance between X-ray lattice faces specified therein.

SUMMARY OF THE INVENTION

It is an object of the invention to provide a process for the catalytic disproportionation of methylnaphthalenes to provide a mixture of naphthalene and dimethylnaphthalenes.

It is a particular object of the present invention to effect the catalytic disproportionation of a feedstock containing at least one methylnaphthalene with high selectivity for the 2,6-dimethylnaphthalene isomer and relatively little of the more highly substituted, e.g., tri- and tetra-, methylnaphthalenes.

By way of realizing the foregoing and other objects of the invention, a process for the disproportionation of a methylnaphthalene is provided which comprises contacting at least one methylnaphthalene under disproportionation reaction conditions with a disproportionation catalyst to provide a product containing naphthalene and at least one dimethylnaphthalene, said disproportionation catalyst comprising a synthetic porous crystalline material characterized by an X-ray diffraction pattern including interplanar d-spacings at 12.36±0.4, 11.03±0.2, 8.83±0.14, 6.18±0.12, 6.00±0.10, 4.06±0.07, 3.91±0.07 and 3.42±0.06 Angstroms.

While the catalytic disproportionation process of this invention can provide all 10 isomers of dimethylnaphthalene, it is relatively selective for the production of 2,6-dimethylnaphthalene which is the precursor of 2,6-naphthalenedicarboxylic acid, a valuable monomer for the production of polyester. Most importantly, the process affords the production of dimethylnaphthalenes without significant production of the more highly substituted and commercially less valuable methylnaphthalenes such as trimethylnaphthalenes and tetramethylnaphthalenes.

DESCRIPTION OF SPECIFIC EMBODIMENTS

The entire contents of applications Ser. Nos. 254,524; 98,176; and 890,268 are incorporated herein by reference.

Of the methylnaphthalenes which can undergo catalytic disproportionation in accordance with the present invention, 2-methylnaphthalene is preferred. Where mixtures of methylnaphthalenes are employed, it is preferred that they contain substantial quantities of 2-methylnaphthalene, e.g., in amount of at least about 20 weight percent, and preferably at least about 50 weight percent, of the total weight of methylnaphthalenes present in the feed. In its calcined form, the synthetic porous crystalline material component employed in the catalyst composition used in the process of this invention is characterized by an X-ray diffraction pattern including the following lines:

TABLE A

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

Alternatively, it may be characterized by an X-ray diffraction pattern in its calcined form including the following lines:

TABLE B

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form may be characterized by an X-ray diffraction pattern including the following lines:

TABLE C

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

Most specifically, it may be characterized in its calcined form by an X-ray diffraction pattern including the following lines:

TABLE D

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_o$, where $I_o$ is the intensity of the strongest line or peak, and d (obs.) the interplanar spacing in Angstrom Units (A), corresponding to the recorded lines, were determined. In Tables A-D, the relative intensities are given in terms of the symbols W=weak, M=medium, S=strong, VS=very strong. In terms of intensities, these may be generally designated as follows:

W=0-20
M=20-40
S=40-60
VS=60-100

It should be understood that these X-ray diffraction patterns are characteristic of all species of the zeolite. The sodium form as well as other cationic forms reveal substantially the same pattern with some minor shifts in interplanar spacing and variation in relative intensity. Other minor variations can occur depending on the ratio of structural components, e.g. silicon to aluminum mole ratio of the particular sample, as well as its degree of thermal treatment.

Examples of such porous crystalline materials include the PSH-3 composition of U.S. Pat. No. 4,439,409, incorporated herein by reference, and MCM-22.

Zeolite MCM-22 has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

wherein R is an organic component. The Na and R components are associated with the zeolite as a result of their presence during crystallization, and are easily removed by post-crystallization methods hereinafter more particularly described.

Zeolite MCM-22 is thermally stable and exhibits a high surface area greater than about 400 m²/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the alkylation catalyst composition herein without having to first undergo an exchange step. To the extent desired, however, the original sodium cations of the as-synthesized material can be replaced in accordance with techniques well known in the art, at least in part, by ion exchange with other cations. Preferred replacement cations include metal ions, hydrogen ions, hydrogen precursor, e.g., ammonium, ions and mixtures thereof. Particularly preferred cations are those which tailor the activity of the catalyst for methylnaphthalene disproportionation. These include hydrogen, rare earth metals and metals of Groups IIA, IIIA, IVA, IB, IIB, IIIB, IVB and VIII of the Periodic Table of the Elements.

In its calcined form, zeolite MCM-22 appears to be made up of a single crystal phase with little or no detectable impurity crystal phases and has an X-ray diffraction pattern including the lines listed in above Tables A-D.

Prior to its use as disproportionation catalyst, the zeolite crystals should be subjected to thermal treatment to remove part or all of any organic constituent present therein.

The zeolite disproportionation catalyst herein can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be introduced in the catalyst composition by way of co-crystallization, exchanged into the composition to the extent a Group IIIA element, e.g., aluminum, is in the structure, impregnated therein or intimately physically admixed therewith. Such component can be impregnated in, or on, the zeolite such as, for example, by, in the case of platinum, treating the zeolite with a solution containing a platinum metal-containing ion. Thus, suitable platinum compounds for this purpose include chloroplatinic acid, platinous chloride and various compounds containing a platinum amine complex.

The zeolite, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use in the disproportionation process of this invention, the zeolite crystals should be at least partially dehydrated. This can be done by heating the crystals to a temperature in the range of from about 200° C. to about 595° C. in an atmosphere such as air, nitrogen, etc., and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

Zeolite MCM-22 can be prpared from a reaction mixture containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, said reaction mixture having a composition, in terms of mole ratios of oxides, within the following ranges:

| Reactants | Useful | Preferred |
|---|---|---|
| $YO_2/X_2O_3$ | 10-60 | 10-40 |
| $H_2O/YO_2$ | 5-100 | 10-50 |
| $OH^-/YO_2$ | 0.01-1.0 | 0.1-0.5 |
| $M/YO_2$ | 0.01-2.0 | 0.1-1.0 |
| $R/YO_2$ | 0.05-1.0 | 0.1-0.5 |

In a preferred method of synthesizing zeolite MCM-22, the $YO_2$ reactant contains a substantial amount of solid $YO_2$, e.g., at least about 30 wt. % solid $YO_2$. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystal formation from the above mixture and is a distinct improvement over the synthesis method disclosed in U.S. Pat. No. 4,439,409. If another source of oxide of silicon, e.g., Q-Brand (a sodium silicate comprised of about 28.8 wt. % of $SiO_2$, 8.9 wt. % $Na_2O$ and 62.3 wt. % $H_2O$) is used, crystallization may yield little if any MCM-22 crystalline material and impurity phases of other crystal structures, e.g., ZSM-12, may be produced. Preferably, therefore, the $YO_2$, e.g., silica, source contains at least about 30 wt. % solid $YO_2$, e.g., silica, and more preferably at least about 40 wt. % solid $YO_2$, e.g., silica. Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals based on the total weight of the crystalline product formed.

The zeolite crystals can be shaped into a wide variety of particle sizes. Generally speaking, the particles can be in the form of a powder, a granule, or a molded product such as an extrudate having a particle size sufficient to pass through a 2 mesh (Tyler) screen and be substantially retained on a 400 mesh (Tyler) screen. In cases where the catalyst is molded, such as by extrusion, the crystals can be extruded before drying or partially dried and then extruded.

It may be desired to incorporate the zeolite crystalline material with another material which is resistant to the temperatures and other conditions employed in the disproportionation process of this invention. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the zeolite, i.e., combined therewith or present during its synthesis, which itself is catalytically active may change the conversion and/or selectivity of the catalyst. Inactive materials suitably serve as diluents to control the amount of conversion so that dimethylnaphthalene disproportionation products can be obtained economically and orderly without employing other means for controlling the rate of reaction. These materials may be incorporated into naturally occurring clays, e.g., bentonite and kaolin, to improve the crush strength of the catalyst under commercial disproportionation operating conditions. Said materials, i.e., clays, oxides, etc., function as binders for the catalyst. It is desirable to provide a catalyst having good crush strength because in commercial use, it is desirable to prevent the catalyst from breaking down into powder-like materials. These clay binders have been employed normally only for the purpose of improving the crush strength of the catalyst.

Naturally occurring clays which can be composited with the zeolite crystals include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the zeolite also include inorganic oxides, notably alumina.

In addition to the foregoing materials, the zeolite crystals can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. It may also be advantageous to provide at least a part of the foregoing matrix materials in colloidal form so as to facilitate extrusion of the bound catalyst component(s).

The relative proportions of finely divided crystalline material and inorganic oxide matrix vary widely, with the crystal content ranging from about 1 to about 95 percent by weight and more usually, particularly when the composite is prepared in the form of beads, in the range of about 2 to about 80 weight percent of the composite.

The stability of the zeolite catalyst may be increased by steaming, with suitable steam stabilization conditions including contacting the catalyst with, for example, 5–100% steam at a temperature of at least 300° C. (e.g. 300°–650° C.) for at least one hour (e.g. 1–200 hours) at a pressure of 100–2,500 kPa. In a more particular embodiment, the catalyst can be made to undergo steaming with 75–100% steam at 315°–500° C. and atmospheric pressure for 2–25 hours.

The methylnaphthalene disproportionation process of this invention is conducted such that the feedstock containing methylnaphthalene(s) is brought into contact with the zeolite catalyst composition in a suitable reaction zone such as, for example, in a flow reactor containing a fixed bed of the catalyst composition, under effective disproportionation conditions. Such conditions include a temperature of from about 300° to about 675° C., and preferably from about 375° to about 575° C., a pressure of from about atmospheric to about 2000 psig and preferably from about 20 to about 1000 psig and a feed weight hourly space velocity (WHSV) of from about 0.1 to about 500 hr$^{-1}$ and preferably from about 0.5 to about 100 hr$^{-1}$. The WHSV is based upon the weight of the catalyst composition employed, i.e., the total weight of active catalyst (and binder if present). The feedstock can be in either the vapor phase or the liquid phase and can be neat, i.e., free from intentional admixture or dilution with other material, or it can be brought into contact with the zeolite catalyst composition with the aid of carrier gases or diluents such as, for example, hydrogen or nitrogen.

The disproportionation process described herein can be carried out as a batch-type, semi-continuous or continuous operation utilizing a fixed or moving bed catalyst system. A preferred embodiment entails use of a catalyst zone wherein the methylnaphthalene charge is passed concurrently or countercurrently through a moving bed of particle-form catalyst. The latter, after use, is conducted to a regeneration zone where coke is burned from the catalyst in an oxygen-containing atmosphere (such as air) at elevated temperature, after which the regenerated catalyst is recycled to the conversion zone for further contact with the organic reactants.

In order to more fully illustrate the disproportionation process of this invention and the manner of practicing same, the following examples are presented. In examples illustrative of the synthesis of zeolite catalyst, whenever sorption data are set forth for comparison of sorptive capacities for water, cyclohexane and/or n-hexane, they were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr of cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. Zeolite MCM-22 always exhibits Equilibrium Adsorption values of greater than about 10 wt. % for water vapor, greater than about 4.5 wt. %, usually greater than about 7 wt. % for cyclohexane vapor and greater than about 10 wt. % for n-hexane vapor. These vapor sorption capacities are a notable distinguishing feature of zeolite MCM-22 and are preferred for the zeolite component of the catalyst for use herein.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec$^{-1}$). The Alpha Test is described in U.S. Pat. No. 3,354,078, in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

EXAMPLE 1

One part of sodium aluminate (43.5% $Al_2O_3$, 32.2% $Na_2O$, 25.6% $H_2O$) was dissolved in a solution containing 1 part of 50% NaOH solution and 103.13 parts $H_2O$. To this was added 4.50 parts hexamethyleneimine. The resulting solution was added to 8.55 parts of Ultrasil, a precipitated, spray-dried silica (about 90% $SiO_2$).

The reaction mixture had the following composition, in mole ratios:

$SiO_2/Al_2O_3 = 30.0$
$OH^-/SiO_2 = 0.18$
$H_2O/SiO_2 = 44.9$
$Na/SiO_2 = 0.18$
$R/SiO_2 = 0.35$ where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table E. The sorption capacities of the calcined material were measured to be:

| | |
|---|---|
| $H_2O$ | 15.2 wt. % |
| Cyclohexane | 14.6 wt. % |
| n-Hexane | 16.7 wt. % |

The surface area of the calcined crystalline material was measured to be 494 m$^2$/g.

The chemical composition of the uncalcined material was determined to be as follows:

| Component | wt. % |
|---|---|
| $SiO_2$ | 66.9 |
| $Al_2O_3$ | 5.40 |
| Na | 0.03 |
| N | 2.27 |
| Ash | 76.3 |

$SiO_2/Al_2O_3$, mole ratio = 21.1

TABLE E

| Degrees 2-Theta | Interplanar d-Spacing (A) | $I/I_o$ |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test and was found to have an Alpha Value of 224.

EXAMPLES 3–5

Three separate synthesis reaction mixtures were prepared with compositions indicated in Table F. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days respectively in stainless steel autoclaves at autogenous pressure. Solids were separated from any unreacted components by filtration and then water washed, followed by drying at 120° C. The product crystals were analyzed by X-ray diffraction, sorption, surface area and chemical analyses. The results of the sorption, surface area and chemical analyses are presented in Table F. The sorption and surface area measurements were of the calcined product.

TABLE F

| Example | 3 | 4 | 5 |
|---|---|---|---|
| Synthesis Mixture, mole ratios | | | |
| $SiO_2/Al_2O_3$ | 30.0 | 30.0 | 30.0 |
| $OH^-/SiO_2$ | 0.18 | 0.18 | 0.18 |
| $H_2O/SiO_2$ | 19.4 | 19.4 | 44.9 |
| $Na/SiO_2$ | 0.18 | 0.18 | 0.18 |
| $R/SiO_2$ | 0.35 | 0.35 | 0.35 |
| Product Composition, Wt. % | | | |
| $SiO_2$ | 64.3 | 68.5 | 74.5 |
| $Al_2O_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| $SiO_2/Al_2O_3$, mole ratio | 22.5 | 20.9 | 26.0 |
| Adsorption, Wt. % | | | |
| $H_2O$ | 14.9 | 13.6 | 14.6 |
| Cyclohexane | 12.5 | 12.2 | 13.6 |
| n-Hexane | 14.6 | 16.2 | 19.0 |
| Surface Area, $m^2/g$ | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and 187, respectively.

EXAMPLE 7

To demonstrate a further preparation of the present zeolite, 4.49 parts of hexamethyleneimine was added to a solution containing 1 part of sodium aluminate, 1 part of 50% NaOH solution and 44.19 parts of $H_2O$. To the combined solution were added 8.54 parts of Ultrasil silica. The mixture was crystallized with agitation at 145° C. for 59 hours and the resultant product was water washed and dried at 120° C.

Product chemical composition, surface area and adsorption analyses results were as set forth in Table G:

TABLE G

| Product Composition (uncalcined) | |
|---|---|
| C | 12.1 wt. % |
| N | 1.98 wt. % |
| Na | 640 ppm |
| $Al_2O_3$ | 5.0 wt. % |
| $SiO_2$ | 74.9 wt. % |
| $SiO_2/Al_2O_3$, mole ratio 25.4 | |
| Adsorption, wt. % | |
| Cyclohexane | 9.1 |
| N-Hexane | 14.9 |
| $H_2O$ | 16.8 |
| Surface Area, $m^2/g$ | 479 |

EXAMPLE 8

Twenty-five grams of solid crystal product from Example 7 were calcined in a flowing nitrogen atmospheres at 538° C. for 5 hours, followed by purging with 5% oxygen gas (balance $N_2$) for another 16 hours at 538° C.

Individual 3 g samples of the calcined material were ion-exchanged with 100 ml of 0.1N TEABr, TPABr and $LaCl_3$ solution separately. Each exchange was carried out at ambient temperature for 24 hours and repeated three times. The exchanged samples were collected by filtration, water-washed to be halide-free and dried. The compositions of the exchanged samples are tabulated below.

| Exchange Ions Ionic Composition, wt. % | TEA | TPA | La |
|---|---|---|---|
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the zeolite had very good stability under severe hydrothermal treatment.

EXAMPLE 11

This example illustrates the preparation of the present zeolite where X in the general formula, supra, is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:

$SiO_2/B_2O_3 = 6.1$
$OH^-/SiO_2 = 0.06$
$H_2O/SiO_2 = 19.0$
$K/SiO_2 = 0.06$
$R/SiO_2 = 0.30$ where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 540° C. and found to have the following sorption capacities:

| $H_2O$ | 11.7 wt. % |
|---|---|
| Cyclohexane | 7.5 wt. % |
| n-Hexane | 11.4 wt. % |

The surface area of the calcined crystalline material was measured (BET) to be 405 $m^2/g$.

The chemical composition of the uncalcined material was determined to be as follows:

| N | 1.94 wt. % |
|---|---|
| Na | 175 ppm |
| K | 0.60 wt. % |
| Boron | 1.04 wt. % |
| $Al_2O_3$ | 920 ppm |
| $SiO_2$ | 75.9 wt. % |
| Ash | 74.11 wt. % |
| $SiO_2/Al_2O_3$, molar ratio = 1406 | |
| $SiO_2/(Al + B)_2O_3$, molar ratio = 25.8 | |

EXAMPLE 12

A portion of the calcined crystalline product of Example 11 was treated with NH$_4$Cl and again calcined. The final crystalline product was tested in the Alpha Test and found to have an Alpha Value of 1.

EXAMPLE 13

This example illustrates another preparation of the zeolite in which X of the general formula, supra, is boron. Boric acid, 2.23 parts, was added to a solution of 1 part of 50% NaOH solution and 73.89 parts H$_2$O. To this solution was added 15.29 parts of HiSil silica followed by 6.69 parts of hexamethyleneimine. The reaction mixture had the following composition in mole ratios:

SiO$_2$/B$_2$O$_3$ = 12.3
OH$^-$/SiO$_2$ = 0.056
H$_2$O/SiO$_2$ = 18.6
K/SiO$_2$ = 0.056
R/SiO$_2$ = 0.30 where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

| | |
|---|---|
| H$_2$O | 14.4 wt. % |
| Cyclohexane | 4.6 wt. % |
| n-Hexane | 14.0 wt. % |

The surface area of the calcined crystalline material was measured to be 438 m$^2$/g.

The chemical composition of the uncalcined material was determined to be as follows:

| Component | Wt. % |
|---|---|
| N | 2.48 |
| Na | 0.06 |
| Boron | 0.83 |
| Al$_2$O$_3$ | 0.50 |
| SiO$_2$ | 73.4 |

SiO$_2$/Al$_2$O$_3$, molar ratio = 249
SiO$_2$/(Al + B)$_2$O$_3$, molar ratio = 28.2

EXAMPLE 14

A portion of the calcined crystalline product of Example 13 was tested in the Alpha Test and found to have an Alpha Value of 5.

EXAMPLE 15

This Example illustrates the use of zeolite MCM-22 in the disproportionation of 2-methylnaphthalenes. The zeolite was prepared by adding adding 4.49 parts hexamethyleneimine to a mixture containing 1.00 part sodium aluminate, 1.00 part 50% NaOH, 8.54 parts Ultrasil VN3 and 44.19 parts deionized H$_2$O. The reaction mixture was heated to 143° C. (290° F.) and stirred in an autoclave at that temperature for crystallization. After full crystallinity was achieved, the majority of the hexamethyleneimine was removed from the autoclave by controlled distillation and the zeolite crystals separated from the remaining liquid by filtration, washed with deionized H$_2$O and dried. A portion of the zeolite crystals was then combined with Al$_2$O$_3$ to form a mixture of 65 parts, by weight, zeolite and 35 parts Al$_2$O$_3$. Water was added to this mixture to allow the resulting catalyst to be formed into extrudates. The catalyst was activated by calcining in nitrogen at 540° C. (1000° F.), followed by aqueous ammoninum nitrate exchange and calcining in air at 540° C. (1000° F.).

The resultant catalyst was charged to a reactor and the reactor was pressurized to 4930 kPa (700 psig) with hydrogen and pre-heated to 450° C. The reactor temperature was reduced to 400° C. and 2-methylnaphthalene was fed to the reactor concurrently with H$_2$. Process conditions were: WHSV=2, H$_2$/2-methylnapthalene (molar)=10, and 4930 kPa (700 psig). The reactor was allowed to equilibrate for 10 hours and after 24 hours, the reaction products were collected and analyzed. The reactor temperature was subsequently raised to 450° C. and 498° C. and similar analyses were made. Table H below summarizes the results of the product analyses.

TABLE H

| Days-on-Stream | 1 | 3 | 5 |
|---|---|---|---|
| Temperature, °C. | 400 | 450 | 498 |
| Product Composition, wt. % | | | |
| Naphthalene | 2.00 | 6.47 | 13.37 |
| 2-Methylnaphthalene | 78.88 | 57.57 | 52.50 |
| 1-Methylnaphthalene | 15.04 | 26.53 | 21.21 |
| Dimethylnaphthalenes | 1.73 | 6.15 | 9.55 |
| 2,6-Dimethylnaphthalene | 0.29 | 0.90 | 1.56 |
| 2,7-Dimethylnaphthalene | 0.25 | 0.95 | 1.39 |
| 1,6-Dimethylnaphthalene | 0.46 | 1.75 | 2.89 |
| 2,3-Dimethylnaphthalene | 0.18 | 0.40 | 0.66 |
| Other Dimethylnaphthalene | 0.55 | 2.15 | 3.05 |
| Tri- and tetra-methylnaphthalenes | 0.28 | 0.67 | 0.77 |
| Other Compounds* | 2.07 | 2.61 | 2.61 |
| Conversion of methylnaphthalene (MN), wt. % | 6.1 | 15.9 | 26.4 |
| Product Selectivities, wt. % | | | |
| DMN (dimethylnaphthalene) | 28.4 | 38.7 | 36.1 |
| 2,6-DMN | 4.8 | 5.7 | 5.9 |
| 2,6- and 2,7-DMN | 8.9 | 11.6 | 11.2 |
| C$_{13}$+ | 4.6 | 4.2 | 2.9 |
| DMN/Naphthalene × 100 | 86.6 | 95.0 | 71.4 |
| 2,6-DMN/Total DMN × 100 | 16.8 | 14.7 | 16.4 |
| 2,6- + 2,7-DMN/Total DMN × 100 | 31.0 | 30.1 | 31.0 |
| MN Isomerization (%) | 16.0 | 31.5 | 28.8 |
| 2-MN/1-MN | 19.1 | 46.1 | 40.4 |

*Includes small amounts of methane, ethylnaphthalenes and other compounds.

EXAMPLE 16 (COMPARATIVE)

A 65% ZSM-5/35% Al$_2$O$_3$ extrudate was crushed, sized to 24/40 mesh and charged to a reactor. Properties of this catalyst are set forth in Table I as follows:

TABLE I

| Catalyst Properties | |
|---|---|
| Surface Area, m$^2$/g | 338 |
| Density, g/cc | |
| Packed | 0.566 |
| Particle | 0.914 |
| Real | 2.629 |
| Pore Volume, cc/g | 0.714 |
| Pore Volume, Å | 85 |
| Ash, wt. % @ 1000° C. | 92.23 |
| Alpha Value | 246 |

The reactor was pressurized to 4930 kPa (700 psig) with hydrogen and pre-heated to 450° C. The reactor temperature was reduced to 400° C. and 2-methylnaphthalene was fed to the reactor concurrently with H$_2$. Process conditions were as in Example 15. The reactor was allowed to equilibrate for 10 hours and after 5 hours, the reaction products were collected and analyzed. The ZSM-5 catalyst of this example tended to age more rapidly than the catalyst of Example 15. Over the course of the next 48 hours, the reactor temperature was raised to 497° C. and 548° C. Analyses of the products are set forth in Table J as follows:

TABLE J

| Days-on-Stream | 1 | 2 | 3 |
|---|---|---|---|
| Temperature, °C. | 400 | 497 | 548 |
| Product Composition, wt. % | | | |
| Naphthalene | 7.30 | 9.24 | 17.94 |
| 2-Methylnaphthalene | 61.10 | 57.06 | 42.91 |
| 1-Methylnaphthalene | 25.66 | 20.27 | 18.03 |
| Dimethylnaphthalenes | 3.27 | 8.05 | 10.04 |
| 2,6-Dimethylnaphthalene | 0.68 | 1.31 | 1.74 |
| 2,7-Dimethylnaphthalene | 0.73 | 1.44 | 1.85 |
| 1,6-Dimethylnaphthalene | 0.89 | 2.44 | 3.09 |
| 2,3-Dimethylnaphthalene | 0.23 | 1.31 | 1.71 |
| Other Dimethylnaphthalene | 0.74 | 1.55 | 1.65 |
| Tri- and tetra-methylnaphthalenes | 1.32 | 2.65 | 3.18 |
| Other Compounds* | 1.35 | 2.73 | 7.90 |
| Conversion of MNs, wt. % | 13.2 | 22.7 | 39.1 |
| Product Selectivities, wt. % | | | |
| DMN (dimethylnaphthalene) | 24.7 | 35.5 | 25.7 |
| 2,6-DMN | 5.1 | 5.8 | 4.5 |
| 2,6- and 2,7-DMN | 10.7 | 12.1 | 9.2 |
| $C_{13}{}^+$ | 10.0 | 11.7 | 8.1 |
| DMN/Naphthalene × 100 | 44.8 | 87.1 | 56.0 |
| 2,6-DMN/Total DMN × 100 | 20.8 | 16.3 | 17.0 |
| 2,6- + 2,7-DMN/Total DMN | 43.1 | 34.2 | 35.8 |
| MN Isomerization | 29.6 | 26.2 | 29.6 |
| 2-MN/1-MN | 42.0 | 35.5 | 42.0 |

*Includes small amounts of methane, ethylnaphthalenes and other compounds.

A comparison of the data in Table H of Example 15 and Table J of this example shows that the catalyst of the invention is more selective for the production of dimethylnaphthalenes and that the difference in DMN selectivities is accounted for in the larger amount of tri- and tetramethylnaphthalenes ($C_{13}+$) produced by ZSM-5. From gas chromatographic analysis, it is further apparent that the catalyst of the present process is significantly more selective for the production of dimethylnaphthalenes than ZSM-5, dimethylnaphthalene losses to the tri- and tetramethylnapahthalenes being much lower with the present catalyst.

What is claimed is:

1. A process for the disproportionation of methylnaphthalenes which comprises contacting at least one methylnaphthalene under disproportionation reaction conditions with a disproportionation catalyst to provide a product containing naphthalene and at least one dimethylnaphthalene isomer, said disproportionation catalyst comprising a synthetic porous crystalline material characterized by an X-ray diffraction pattern including values substantially as set forth in Table A of the specification.

2. The process of claim 1 wherein the synthetic porous crystalline material is characterized by an X-ray diffraction pattern including values substantially as set forth in Table B of the specification.

3. The process of claim 1 wherein the synthetic porous crystalline material is characterized by an X-ray diffraction pattern including values substantially as set forth in Table C of the specification.

4. The process of claim 1 wherein the synthetic porous crystalline material is characterized by an X-ray diffraction pattern including values substantially as set forth in Table D of the specification.

5. The process of claim 1 wherein the synthetic porous crystalline material has a composition comprising the molar relationship $$X_2O_3:(n)YO_2,$$

wherein n is at least about 10, X is a trivalent element and Y is a tetravelent element.

6. The process of claim 1 wherein the synthetic porous crystalline material possesses equilibrium adsorption capacities of greater than about 4.5 wt. % for cyclohexane vapor and greater than about 10 wt. % for n-hexane vapor.

7. The process of claim 5 wherein X is selected from the group consisting of aluminum, boron, gallium and combinations thereof and Y is selected from the group consisting of silicon, germanium and combinations thereof.

8. The process of claim 5 wherein X comprises aluminum and Y comprises silicon.

9. The process of claim 1 wherein said synthetic porous crystalline material has been treated to replace original cations, at least in part, with a cation or mixture of cations selected from the group consisting of hydrogen, hydrogen precursors, rare earth metals, and metals of Groups IIA, IIIA, IVA, IB, IIB, IIIB, IVB, VIB and VIII of the Periodic Table.

10. The process of claim 1 wherein said synthetic porous crystalline material has been thermally treated at a temperature up to about 925° C. in the presence or absence of steam.

11. The process of claim 9 wherein said synthetic porous crystalline material has been thermally treated at a temperature up to about 925° C. in the presence or absence of steam.

12. The process of claim 1 wherein said synthetic porous crystalline material is combined with a matrix material.

13. The process of claim 12 wherein said matrix material is selected from the group consisting of silica-containing material, alumina-containing material, zirconia-containing material, titania-containing material, magnesia-containing material, beryllia-containing material, thoria-containing material, and combinations thereof.

14. The process of claim 12 wherein the catalyst is provided in the form of extrudate, beads or fluidizable microspheres.

15. The process of claim 1 wherein the methylnaphthalene is 2-methylnaphthalene.

16. The process of claim 1 wherein a mixture of methylnaphthalenes is disproportionated with 2-methylnaphthalene representing at least about 20 weight percent of the total methylnaphthalenes.

17. The process of claim 1 wherein a mixture of methylnaphthalenes is disproportionated with 2-methylnaphthalene representing at least about 50 weight percent of the total methylnaphthalenes.

18. The process of claim 1 wherein the disproportionation conditions include a temperature of from about 300° to about 675° C., a pressure of from about atmospheric to about 2000 psig and a weight hourly space velocity (WHSV) of from about 0.1 to about 500 hr$^{-1}$.

19. The process of claim 1 wherein the disproportionation conditions include a temperature of from about 375° to about 575° C., a pressure of from about 200 to about 1000 psig and a weight hourly space velocity (WHSV) of from about 0.5 to about 100 hr$^{-1}$.

* * * * *